US012082938B2

(12) United States Patent
Smith et al.

(10) Patent No.: US 12,082,938 B2
(45) Date of Patent: Sep. 10, 2024

(54) PHOTOACOUSTIC VOLTAGE INDICATORS (71) Applicants: Barbara Smith, Tempe, AZ (US); Christopher Miranda, Mesa, AZ (US)

(72) Inventors: Barbara Smith, Tempe, AZ (US); Christopher Miranda, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 171 days.

(21) Appl. No.: 17/533,278

(22) Filed: Nov. 23, 2021

(65) Prior Publication Data
US 2022/0160289 A1 May 26, 2022

Related U.S. Application Data (60) Provisional application No. 63/117,004, filed on Nov. 23, 2020.

(51) Int. Cl.
*A61B 5/00* (2006.01)
*G01N 15/10* (2006.01)
*G01N 15/01* (2024.01)

(52) U.S. Cl.
CPC .......... *A61B 5/4064* (2013.01); *A61B 5/0095* (2013.01); *G01N 15/1023* (2024.01); *G01N 15/01* (2024.01); *G01N 2015/1006* (2013.01)

(58) Field of Classification Search
CPC .................................................. A61B 5/4064
See application file for complete search history.

(56) References Cited

U.S. PATENT DOCUMENTS 2,761,077 A 8/1956 Harris
5,769,086 A 6/1998 Ritchart
(Continued)

FOREIGN PATENT DOCUMENTS

DE 102015114670 3/2017
EP 3118608 1/2017
WO 9903399 A1 1/1999

OTHER PUBLICATIONS

Rasheed et al. ("Photoacoustic sensing of bioelectrical activity" Dissertation, George Mason University, 2008) (Year: 2008).*
(Continued)

*Primary Examiner* — Joseph M Santos Rodriguez
(74) *Attorney, Agent, or Firm* — Riverside Law LLP (57) ABSTRACT A system for measuring a membrane potential is disclosed. The system comprises a photoacoustic probe including a laser and an ultrasound transducer. The laser is configured to emit a light signal at one or more wavelengths to a neuronal cell. The neuronal cell may comprise a voltage-sensitive protein configured to absorb the light signal in a voltage-dependent manner. The ultrasound transducer is configured to receive a photoacoustic signal from the voltage-sensitive protein in response to absorbing the light signal. The system further comprises a processor configured to receive the photoacoustic signal from the ultrasound transducer and calculate a membrane potential of the neuron based on the photoacoustic signal. Methods of measuring a membrane potential and biomaterials related to the voltage-sensitive protein are also disclosed herein.

15 Claims, 4 Drawing Sheets

(56) References Cited

U.S. PATENT DOCUMENTS

| | | | |
|---|---|---|---|
| 5,916,210 | A | 6/1999 | Winston |
| 9,594,075 | B2 | 3/2017 | Eggan |
| 10,352,945 | B2 | 7/2019 | Cohen |
| 10,405,750 | B2 | 9/2019 | Wang |
| 11,045,169 | B2 | 6/2021 | Smith |
| 2007/0132846 | A1 | 6/2007 | Broad |
| 2008/0064921 | A1 | 3/2008 | Larkin |
| 2008/0091104 | A1 | 4/2008 | Abraham |
| 2008/0312561 | A1 | 12/2008 | Chauhan |
| 2009/0048515 | A1 | 2/2009 | Suri |
| 2010/0001171 | A1 | 1/2010 | Matsuo |
| 2010/0245769 | A1 | 9/2010 | Zhang |
| 2010/0268042 | A1 | 10/2010 | Wang |
| 2011/0098572 | A1 | 4/2011 | Chen |
| 2011/0282192 | A1 | 11/2011 | Axelrod |
| 2013/0190595 | A1 | 7/2013 | Oraevsky |
| 2015/0173618 | A1 | 6/2015 | Kusukame |
| 2015/0216420 | A1 | 8/2015 | Oraevsky |
| 2016/0150968 | A1 | 6/2016 | Imai |
| 2016/0213258 | A1 | 7/2016 | Lashkari |
| 2016/0242650 | A1 | 8/2016 | Chen |
| 2017/0138926 | A1 | 5/2017 | Chubykin |
| 2017/0327841 | A1 | 11/2017 | Deisseroth |
| 2017/0367682 | A1 | 12/2017 | Smith |
| 2018/0008243 | A1 | 1/2018 | Irisawa |
| 2018/0057396 | A1 | 3/2018 | Li |
| 2018/0078235 | A1 | 3/2018 | Irisawa |
| 2018/0177408 | A1 | 6/2018 | Irisawa |
| 2018/0177409 | A1 | 6/2018 | Irisawa |
| 2018/0220895 | A1 | 8/2018 | Masaki |
| 2018/0259370 | A1 | 9/2018 | Fontaine |
| 2019/0000377 | A1 | 1/2019 | Lei |
| 2019/0021598 | A1 | 1/2019 | Eom |
| 2019/0046159 | A1 | 2/2019 | Smith |
| 2019/0110691 | A1 | 4/2019 | Smith |
| 2019/0282069 | A1 | 9/2019 | Smith |
| 2020/0163612 | A1 | 5/2020 | Ntziachristos |
| 2021/0022680 | A1 | 1/2021 | Harris |
| 2021/0275140 | A1 | 9/2021 | Smith |
| 2021/0353782 | A1 | 11/2021 | Smith |
| 2021/0402040 | A1 | 12/2021 | Botts |
| 2022/0202293 | A1 | 6/2022 | Kim |

OTHER PUBLICATIONS

Kralj et al. ("Optical recording of action potentials in mammalian neurons using microbial rhodopsin" Nat Methods vol. 9(1) p. 90-95, 2012 (Year: 2012).*

Laufer et al "In vitro characterization of genetically expressed absorbing proteins using photoacoustic spectroscopy") . . . (Year: 2013).*

Salvesen, H. et al., "Independent prognostic importance of microvessel density in endometrial carcinoma", British Journal of Cancer, Apr. 1998, vol. 77, No. 7, pp. 1140-1144 <DOI:10.1038/bjc.1998.189>.

Scarcelli et al., Conformal Brillouin Microscopy for Three-Dimensional Mechanical Imaging, 12 pages.

Schwarz, M. et al., "Three-dimensional multispectral optoacoustic mesoscopy reveals melanin and blood oxygenation in human skin in vivo", Journal of Biophotonics, Jan. 2016, vol. 9, No. 1-2, pp. 55-60 <DOI:10.1002/jbio.201500247>.

Sethuraman, S. et al., "Intravascular Photoacoustic Imaging Using an IVUS Imaging Catheter", IEEE Transactions on Ultrasonics, Ferroelectrics, and Frequency Control, May 2007, vol. 54, No. 5, pp. 978-986 <DOI:10.1109/TUFFC.2007.343>.

Shao et al., "Spatially-Resolved Brillouin Spectroscopy Reveals Biomechanical Abnormalities in Mild to Advanced Keratoconus in Vivo," Sci Rep 9, 7467 (2019).

Shelton et al., Picosecond Ultrasonic Measurement of the Velocity of Phonons in Water, Physica Status Solidi (b), 242(7):1379-1382, 2005.

Siegal, R. et al., "Cancer statistics, 2016", CA-Cancer Journal, Jan./Feb. 2016, vol. 66, No. 1, pp. 7-30 <DOI:10.3322/caac.21332>.

Siphanto, R. et al., "Serial noninvasive photoacoustic imaging of neovascularization in tumor angiogenesis", Optics Express, Jan. 2005, vol. 13, No. 1, pp. 89-95 <DOI:10.1364/OPEX.13.000089>.

Smith-Bindman, R. et al., "Endovaginal ultrasound to exclude endometrial cancer and other endometrial abnormalities", JAMA, Nov. 1998, vol. 280, No. 17, pp. 1510-1517.

Stewart, E. et al., "Uterine Fibroids", Lancet, Jan. 2001, vol. 357, No. 9252, pp. 293-298 <DOI:10.1016/S0140-6736(00)03622-9>.

Subach et al., Directed molecular evolution to design advanced red fluorescent proteins. Nature methods, 8(12):1019, 2011.

Suk et al., "Closed-Loop Real-Time Imaging Enables Fully Automated Cell-Targeted Patch-Clamp Neural Recoding In Vivo," Neuron 95, 1037-1047, Aug. 30, 2017.

Symonds, I., "Ultrasound, hysteroscopy and endometrial biopsy in the investigation of endometrial cancer", Best Practice & Research. Clinical Obstetrics & Gynecology, Jun. 2001, vol. 15, No. 3, pp. 381-391 <DOI: 10.1053/beog.2000.0183>.

Tamai, K. et al., "Diffusion-weighted MR imaging of uterine endometrial cancer", Journal of Magnetic Resonance Imaging: JMRI, Sep. 2007, vol. 26, No. 3, pp. 682-687 <DOI:10.1002/jmri.20997>.

Timmermans, A. et al., "Endometrial thickness measurement for detecting endometrial cancer in women with postmenopausal bleeding: a systematic review and meta-analysis", Obstetrics and Gynecology, Jul. 2010, vol. 116, No. 1, pp. 160-167 <DOI:10.1097/AOG.0b013e3181e3e7e8>.

Tour et al., (2003). Genetically targeted chromophore-assisted light inactivation. Nature biotechnology, 21(12), 1505-1508.

Treeby et al., Photoacoustic tomography in absorbing acoustic media using time reversal. Inverse Problems, 26(11):115003, 2010.

Tsien, New calcium indicators and buffers with high selectivity against magnesium and protons: design, synthesis, and properties of prototype structures. Biochemistry, 19(11):2396-2404, 1980.

Wang, B. et al., "Intravascular photoacoustic imaging of lipid in atherosclerotic plaques in the presence of luminal blood", Optics Letters, Apr. 2012, vol. 37, No. 7, pp. 1244-1246 <DOI:10.1364/OL.37.001244>.

Wang, B. et al., "Intravascular Photoacoustic Imaging", IEEE Journal of Selected Topics in Quantum Electronics, May/Jun. 2010, vol. 16, No. 3, pp. 588-599 <DOI:10.1109/JSTQE.2009.2037023>.

Wang, L. et al., "Photoacoustic Tomography: In Vivo Imaging from Organelles to Organs", Science, Mar. 2012, vol. 335, No. 6075, pp. 1458-1462 <DOI:10.1126/science.1216210>.

Wang, P. et al., "High-speed intravascular photoacoustic imaging of lipid-laden atherosclerotic plaque enabled by a 2-кHz barium nitrite raman laser", Scientific Reports, Nov. 2014, vol. 4, No. 6889, 7 pages <DOI:10.1038/srep06889>.

Wang, X. et al., "Noninvasive imaging of hemoglobin concentration and oxygenation in the rat brain using high-resolution photoacoustic tomography", Journal of Biomedical Optics, Mar./Apr. 2006, vol. 11, No. 2, article 024015 (9 pages) <DOI:10.1117/1.2192804>.

Wissmeyer et al., Looking at sound: optoacoustics with all-optical ultrasound detection. Light: Science & Applications, 7(1):1-16, 2018.

Wright, D. et al., "Contemporary management of endometrial cancer", Lancet, Apr. 2012, vol. 379, No. 9823, pp. 1352-1360 <DOI:10.1016/S0140>.

Wu et al., Dynamic dimensional synthesis of a precision 6-DOF parallel manipulator, 2012 IEEE International Conference on Mechatronics and Automation, DOI: 10.1109/ICMA.2012.6283250, Date of Conference: Aug. 5-8, 2012, Date Added to IEEE Xplore: Aug. 27, 2012 (Year: 2012).

Xu, M. et al., "Photoacoustic imaging in biomedicine", Review of Scientific Instruments, Feb. 2006, vol. 77, No. 4, article 041101 (23 pages) <DOI:10.1063/1.2195024>.

Yang, J. et al., "Photoacoustic Endoscopy", Optics Letters, May 2009, vol. 34, No. 10, pp. 1591-1593.

Yang, J. et al., "Simultaneous functional photoacoustic and ultrasonic endoscopy of internal organs in vivo", Nature Medicine, Aug. 2012, vol. 18, No. 8, pp. 1297-1302 <DOI:10.1038/nm.2823>.

(56) References Cited

OTHER PUBLICATIONS

Yang, J. et al., "Three-dimensional photoacoustic endoscopic imaging of the rabbit esophagus", PLoS One, Apr. 2015, vol. 10, No. 4, article e0120269 (15 pages) <DOI:10.1371/journal.pone.0120269>.

Yang, J. et al., "Volumetric photoacoustic endoscopy of upper gastrointestinal tract: ultrasonic transducer technology development", Proceedings of SPIE, Feb. 2011, vol. 7899, article 78990D (6 pages) <DOI:10.1117/12.875377>.

Yao et al., (2015). High-speed label-free functional photoacoustic microscopy of mouse brain in action. Nature methods, 12(5), 407-410.

Yao, Da-Kang et al. "Photoacoustic measurement of the Grüneisen parameter of tissue." Journal of biomedical optics vol. 19,1 (2014): 17007. doi:10.1117/1.JBO.19.1.017007 (Year: 2014).

Yao, J. et al., "Label-free oxygen-metabolic photoacoustic microscopy in vivo", Journal of Biomedical Optics, Jul. 2011, vol. 16, No. 7, article 076003 (12 pages) <DOI:10.1117/1.3594786>.

Yeh, C. et al., "Microvascular quantification based on contour-scanning photoacoustic microscopy", Journal of Biomedical Optics, Sep. 2014, vol. 19, No. 9, article 096011 (7 pages) <DOI:10.1117/1.JBO.19.9.096011>.

Yu et al., (2003). Detection of Calcium Transients in DrosophilaMushroom Body Neurons with Camgaroo Reporters. Journal of Neuroscience, 23(1), 64-72.

Zacharias et al., (2002). Partitioning of lipid-modified monomeric GFPs into membrane microdomains of live cells. Science, 296(5569), 913-916.

Zhang, E. et al., "A miniature all-optical photoacoustic imaging probe", Proceedings of SPIE, Feb. 2011, vol. 1899, article 78991F (7 pages) <DOI:10.1117/12.874883>.

Zhang, E. et al., "In vivo high-resolution 3D photoacoustic imaging of superficial vascular anatomy", Physics in Medicine and Biology, Feb. 2009, vol. 54, No. 4, pp. 1035-1046 <DOI:10.1088/0031-9155/54/4/014>.

Aguirre, A. et al., "Potential Role of Coregistered Photoacoustic and Ultrasound Imaging in Ovarian Cancer Detection and Characterization", Translational Oncology, Feb. 2011, vol. 4, No. 1, pp. 29-37 <DOI:10.1593/tlo.10187>.

Alcázar, J. et al., "Endometrial blood flow mapping using transvaginal power Doppler sonography in women with postmenopausal bleeding and thickened endometrium", Ultrasound in Obstetrics & Gynecology, Jun. 2003, vol. 21, No. 6, pp. 583-588 <DOI:10.1002/uog.143>.

Alcázar, J. et al., "Intratumoral blood flow analysis in endometrial carcinoma: correlation with tumor characteristics and risk for recurrence", Gynecological Oncology, Feb. 2002, vol. 84, No. 2, pp. 258-262 <DOI:10.1006/gyno.2001.6496>.

Alcázar, J. et al., "Three-dimensional power Doppler ultrasound scanning for the prediction of endometrial cancer in women with postmenopausal bleeding and thickened endometrium", American Journal of Obstetrics and Gynecology, Jan. 2009, vol. 200, No. 1, article 44.e (6 pages) <DOI:10.1016/j.ajog.2008.08.027>.

Alcázar, J. et al., "Three-dimensional ultrasound for assessing women with gynecological cancer: a systematic review", Gynecologic Oncology, Mar. 2011, vol. 120, No. 3, pp. 340-346 <DOI:10.1016/j.ygyno.2010.10.023>.

Amant, F. et al., "Endometrial Cancer", Lancet, Aug. 2005, vol. 366, No. 9484, pp. 491-505 <DOI:10.1016/S0140-6736(05)67063-8>.

Annecchino et al., "Robotic Automation of In Vivo Two-Photon Targeted Whole-Cell Patch-Clamp Electrophysiology," Neuron 95, 1048-1055, Aug. 30, 2017.

Antonsen, S. et al., "MRI, PET/CT and ultrasound in the preoperative staging of endometrial cancer—a multicenter prospective comparative study", Gynecologic Oncology, Feb. 2013, vol. 128, No. 2, pp. 300-308 <DOI:10.1016/j.ygyno.2012.11.025>.

Aytac-Kipergil, E., Demirkiran, A., Uluc, N. et al. Development of a Fiber Laser with Independently Adjustable Properties for Optical Resolution Photoacoustic Microscopy. Sci Rep 6, 38674 (2016). https://doi.org/10.1038/srep38674, Published Dec. 8, 2016 (Year: 2016).

Bai, X. et al., "Intravascular optical-resolution photoacoustic tomography with a 1.1 mm diameter catheter", PLoS One, Mar. 2014, vol. 9, No. 3, article e92463 (6 pages) <DOI:10.1371/journal.pone.0092463>.

Bando et al., Genetic voltage indicators. BMC biology, 17(1):71, 2019.

Bedner, R. et al., "Hysteroscopy with directed biopsy versus dilatation and curettage for the diagnosis of endometrial hyperplasia and cancer in perimenopausal women", European Journal of Gnyaecological Oncology, 2007, vol. 28, No. 5, pp. 400-402.

Bohndiek, S. et al., "Development and application of stable phantoms for the evaluation of photoacoustic imaging instruments", PLoS One, Sep. 2013, vol. 8, No. 9, article e75533 (14 pages) <DOI:10.1371/journal.pone.0075533>.

Burke, W. et al., "Endometrial cancer: a review and current management strategies: part II", Gynecologic Oncology, Aug. 2014, vol. 134, No. 2, pp. 393-402 <DOI:10.1016/j.ygyno.2014.06.003>.

Cheng, W. et al., "Clinical application of intratumoral blood flow study in patients with endometrial carcinoma", Cancer, May 1998, vol. 82, No. 10, pp. 1881-1886 <DOI:10.1002/(SICI)1097-0142(May 15, 1998)82:10%3C1881::AID-CNCR10%3E3.0.CO;2-P>.

Clement, P., "The pathology of uterine smooth muscle tumors and mixed endometrial stromal-smooth muscle tumors: a selective review with emphasis on recent advances", International Journal of Gynecological Pathology, Jan. 2000, vol. 19, No. 1, pp. 39-55.

Davis et al., Viral mutagenesis as a means for generating novel proteins. Journal of virology, 84(3):1625-1630, 2010.

Emoto, M. et al., "Clinical usefulness of color Doppler ultrasound in patients with endometrial hyperplasia and carcinoma", Cancer, Feb. 2002, vol. 94, No. 3, pp. 700-706 <DOI:10.1002/cncr.10208>.

Fluorescent Indicators for Cytosolic Sodium by Akwasi Minta et al.; Pub. The Journal of Biological Chemistry vol. 264, No. 32, Issue of Nov. 15, pp. 19449-19457, 1989 (Year: 1989).

Fyles et al., Photoionophores derived from crown ether polycarboxylic acids: synthesis, ion binding, and spectroscopic characterization. Canadian journal of chemistry, 72(5):1246-1253, 1994.

Gaietta et al., (2002). Multicolor and electron microscopic imaging of connexin trafficking. Science, C70:I81 296(5567), 503-507.

Goldstein, S., "The role of transvaginal ultrasound or endometrial biopsy in the evaluation of the menopausal endometrium", American Journal of Obstetrics and Gynecology, Jul. 2009, vol. 201, No. 1, pp. 5-11 <DOI:10.1016/j.ajog.2009.02.006>.

Hochbaum et al., All-optical electrophysiology in mammalian neurons using engineered microbial rhodopsins. Nature methods, 11(8):825, 2014.

Jansen, K. et al., "Lipid detection in atherosclerotic human coronaries by spectroscopic intravascular photoacoustic imaging", Optics Express, Sep. 2013, vol. 21, No. 18, pp. 21472-21484 <DOI:10.1364/OE.21.021472>.

Jathoul, A. et al., "Deep in vivo photoacoustic imaging of mammalian tissues using a tyrosinase-based genetic reporter", Nature Photonics, Mar. 2015, vol. 9, No. 4, pp. 239-246 <DOI:10.1038/nphoton.2015.22>.

Karpiouk, A. et al., "Feasibility of in vivo intravascular photoacoustic imaging using integrated ultrasound and photoacoustic imaging catheter", Journal of Biomedical Optics, Sep. 2012, vol. 17, No. 9, article 096008 (7 pages) <DOI:10.1117/1.JBO.17.9.096008>.

Keshavarzi, A. et al., "Attenuation coefficient and sound speed in human myometrium and uterine fibroid tumors", Journal of Ultrasound in Medicine, May 2001, vol. 20, No. 5, pp. 473-480 <DOI:10.7863/jum.2001.20.5.473>.

Kim, C. et al., "In Vivo Molecular Photoacoustic Tomography of Melanomas Targeted by Bioconjugated Gold Nanocages", ACS Nano, Jul. 2010, vol. 4, No. 8, pp. 4559-4564 <DOI:10.1021/nn100736c>.

Kodama, J. et al., "Correlation of presenting symptoms and patient characteristics with endometrial cancer prognosis in Japanese women", International Jounral of Gynecology & Obstetrics, Sep. 2005, vol. 91, No. 2, pp. 151-156 <DOI:10.1016/j.ijgo.2005.08.002>.

Kodandaramaiah et al., "Automated Whole-Cell Patch-Clamp Electrophysiology of Neurons In Vivo," Nature Methods vol. 9, No. 6, Jun. 2012, pp. 585-590.

(56) References Cited

OTHER PUBLICATIONS

Kodandaramaiah et al., "Multi-Neuron Intracellular Recording in Vivo Via Interacting Autopatching Robots," Elife 7 (2018): e24656.

Kruger, R. et al., "Dedicated 3D photoacoustic breast imaging", Medical Physics, Nov. 2013, vol. 40, No. 11, article 113301 (8 pages) <DOI:10.1118/1.4824317>.

Kumar et al. Dual-view plane illumination microscopy for rapid and spatially isotropic imaging. Nature protocols, 9(11):2555-2573, 2014.

Lao, Y. et al., "Noninvasive photoacoustic imaging of the developing vasculature during early tumor growth", Physics in Medicine and Biology, Aug. 2008, vol. 53, No. 15, pp. 4203-4212 <DOI:10.1088/0031-9155/53/15/013>.

Lee, C. et al., "Angiogenesis of endometrial carcinomas assessed by measurement of intratumoral blood flow, microvessel density, and vascular endothelial growth factor levels", Obstetrics and Gynecology, Oct. 2000, vol. 96, No. 4, pp. 615-621.

Li, M. et al., "Simultaneous Molecular and Hypoxia Imaging of Brain Tumors in Vivo Using Spectroscopic Photoacoustic Tomography", Proceedings of the IEEE, Mar. 2008, vol. 96, No. 3, pp. 481-489 <DOI:10.1109/JPROC.2007.913515>.

Limited Utility of Acetoxymethyl (AM) Based Intracellular Delivery Systems, in vivo: Interference by Extracellular Esterases; by Paul D. Jobis et al.; Pub. J Microsc. Apr. 2007 ; 226(Pt 1): pp. 74-81. (Year: 2007).

Mallidi, S. et al., "Photoacoustic imaging in cancer detection, diagnosis, and treatment guidance", Trends in Biotechnology, May 2011, vol. 29, No. 5, pp. 213-221 <DOI:10.1016/j.tibtech.2011.01.006>.

Merz, E. et al., "Sonographic size of uterus and ovaries in pre- and postmenopausal women", Ultrasound in Obstetrics & Gynecology, Jan. 1996, vol. 7, No. 1, pp. 38-42 <DOI:10.1046/j.1469-0705.1996.07010038.x>.

Minta et al., Fluorescent indicators for cytosolic sodium. Journal of Biological Chemistry, 264(32):19449-19457, 1989.

Miranda et al. "Photoacoustic micropipette," Applied Phsyics Letters 113(26): 264103 (2018).

Miranda, C. et al., "Intrauterine photoacoustic and ultrasound imaging probe", Journal of Biomedical Optics, Apr. 2018, vol. 23, No. 4, article 046008 (9 pages) <DOI:10.1117/1.JBO.23.4.046008>.

Mishra et al., Near-infrared photoacoustic imaging probe responsive to calcium. Analytical chemistry, 88(22):10785-10789, 2016.

Morice, P. et al., "Endometrial Cancer", Lancet, Mar. 2016, vol. 387, No. 10023, pp. 1094-1108 <DOI:10.1016/S0140-6736(15)00130-0>.

Nakahara et al., "Fluorometric sensing of alkali metal and alkaline earth metal cations by novel photosensitive monoazacryptand derivatives in aqueous micellar solutions," Organic & biomolecular chemistry, 3(9):1787-1794, 2005.

Nicholson, W. et al., "Patterns of ambulatory care use for gynecologic conditions: a national study", American Journal of Obstetrics and Gynecology, Mar. 2001, vol. 184, No. 4, pp. 523-530 <DOI:10.1067/mob.2001.111795>.

Ning, B. et al., "Simultaneous photoacoustic microscopy of microvascular anatomy, oxygen saturation, and blood flow", Optics Letters, Mar. 2015, vol. 40, No. 6, pp. 910-913 <DOI:10.1364/OL.40.000910>.

Piatkevich et al. A robotic multidimensional directed evolution approach applied to fluorescent voltage reporters. Nature chemical biology, 14(4):352-360, 2018.

Pitrone et al., Openspim: an open-access light-sheet microscopy platform. Nature methods, 10(7):598-599, 2013.

Ribatti, D. et al., "Neovascularization and mast cells with tryptase activity increase simultaneously with pathologic progression in human endometrial cancer", American Journal of Obstetrics & Gynecology, Dec. 2005, vol. 193, No. 6, pp. 1961-1965 <DOI:10.1016/j.ajog.2005.04.055>.

* cited by examiner

PHOTOACOUSTIC VOLTAGE INDICATORS

CROSS-REFERENCE TO RELATED APPLICATIONS

This application claims the benefit of priority to U.S. Provisional Application No. 63/117,004 entitled "Photoacoustic Voltage Indicators," filed Nov. 23, 2020, which is incorporated herein by reference in its entirety.

TECHNICAL FIELD

The present disclosure relates generally to methods, systems, and apparatuses related to detecting and measuring the membrane potential of neurons. The disclosed techniques may be applied to various tissues as a research tool, for example, in vitro neural tissue and/or in vivo neural tissue (e.g., brain tissue).

BACKGROUND

The activity of neurons has long been studied to characterize and understand neurological activity. Neurons are electrically excitable cells that serve as a primary component of the nervous system in most animals. Neurons are bundled together to form nerve tracts in the central nervous system and nerves in the peripheral nervous system, thus creating the basic pathway of neurological activity that facilitates communication between different parts of the body to convey information and coordinate actions.

Neurological activity is directly related to changes in membrane potential due to ion flux across the neuron's membrane. In the resting state, a surplus of positively charged ions outside of the cell create a negative concentration gradient across the membrane. In response to a stimulus, some sodium channels open allowing an influx of sodium ions ($Na^+$) that results in depolarization of the cell. A threshold amount of depolarization triggers the opening of voltage-gated sodium channels that allow a massive rush of sodium ions into the cell, thereby causing an action potential to pass across the axon as the depolarization spreads. Thereafter, voltage-gated potassium channels open (while the voltage-gated sodium channels close) and cause an outflow of potassium ions ($K^+$) to repolarize the cell, eventually returning it to the resting potential. Finally, an influx of calcium ions ($Ca^{2+}$) through voltage-gated calcium channels triggers the release of neurotransmitters from the axon terminal to initiate synaptic transmission.

Due to this close relationship between concentration gradients and signal transmission across the neuron, measurement of membrane potential sheds light on neurological activity and facilitates study of nervous system function and disorders thereof. Current approaches to tracking membrane potential in neurons utilize fluorescent ion indicators (FIIs) comprising a metal chelating agent (i.e., a metal chelator) combined with a fluorescent contrast agent (i.e., a genetically encoded fluorophore, imaging dye, etc.). Together, the complex selectively binds a specific metal ion such as $Na^+$ or $Ca^{2+}$ and fluoresces and/or causes a shift in fluorescence in response to enable visualization of the concentration gradient. Although available FIIs have proven useful in visualizing the flow of ions across the neuron membrane, they suffer from several drawbacks. For example, ion indicators provide only an indirect measure of the action potential. Ion indicators are incapable of providing direct measurement due to, among other factors, a delay between the ion flux and the action potential.

Another approach to tracking membrane potential utilizes fluorescence-based transmembrane voltage indicators that are expressed across the membrane of a cell (i.e., genetically encoded voltage indicators or GEVIs). The transmembrane voltage indicators may sense a membrane potential across the membrane and emit a voltage-specific fluorescence response to enable visualization of the membrane potential. For example, a shift in fluorescence may occur in a voltage-specific manner such that measurement of the emitted fluorescence may be used to calculate membrane potential. However, development of fluorescence-based transmembrane voltage indicators has proven very challenging, and, thus, the available options are limited and generally offer poor contrast. Potential for development is limited by the fact that such fluorescence-based approaches require a highly fluorescent molecule, which is a rarer trait that restricts the choice of materials. Quantum yields for most GEVIs are orders of magnitude lower than the most common fluorophores. Thus, there is a need for an improved approach. Even further, the reliance on fluorescence for visualization naturally limits the depth at which imaging can occur.

As such, it would be advantageous to have a method of tracking membrane potential by direct measurement without reliance on fluorescent molecules in order to provide an abundant range of materials for development of indicators. It would be further advantageous to have a voltage indicator configured for high-resolution imaging at greater depths.

SUMMARY

This summary is provided to comply with 37 C.F.R. § 1.73. It is submitted with the understanding that it will not be used to interpret or limit the scope or meaning of the present disclosure.

A system for measuring a membrane potential is provided. The system comprises a photoacoustic probe comprising: a laser configured to emit a light signal at one or more wavelengths to a neuronal cell comprising a voltage-sensitive protein capable of absorbing the light signal in a voltage-dependent manner, and an ultrasound transducer configured to receive a photoacoustic signal from the voltage-sensitive protein in response to absorbing the light signal; a processor; and a non-transitory, computer-readable medium storing instructions that, when executed, cause the processor to: receive the photoacoustic signal from the ultrasound transducer, and calculate, based on the photoacoustic signal, the membrane potential of the neuronal cell.

According to some embodiments, the voltage-sensitive protein comprises a transmembrane protein. According to additional embodiments, the transmembrane protein comprises a rhodopsin.

According to some embodiments, at least one light absorption characteristic of the voltage-sensitive protein is configured to shift based on the membrane potential of the neuronal cell, wherein the instructions that cause the processor to calculate a membrane potential of the neuronal cell comprise instructions that, when executed, cause the processor to: quantify, based on the photoacoustic signal, the at least one light absorption characteristic of the voltage-sensitive protein, and determine, based on the quantified at least one light absorption characteristic, the membrane potential of the neuronal cell. According to additional embodiments, the at least one light absorption characteristic comprises an absorption coefficient of the voltage-sensitive protein, wherein the absorption coefficient is configured to shift based on the membrane potential sensed by the voltage-sensitive protein. According to additional embodiments, the at least one light absorption characteristic comprises a peak absorption wavelength of the voltage-sensitive protein from the one or more wavelengths, wherein the peak absorption wavelength is configured to shift based on the membrane potential sensed by the voltage-sensitive protein. According to additional embodiments, the at least one light absorption characteristic comprises a total absorption value for the voltage-sensitive protein at the one or more wavelengths, wherein the total absorption value is configured to shift based on the membrane potential sensed by the voltage-sensitive protein.

According to some embodiments, the voltage-sensitive protein is configured to absorb light at the one or more wavelengths in the voltage-dependent manner with sensitivity to changes in the membrane potential across a voltage range of about −70 mV to about 30 mV.

According to some embodiments, the voltage-sensitive protein has an extinction coefficient between about 102 M−1 cm−1 to about 104 M−1 cm−1.

According to some embodiments, the voltage-sensitive protein is configured to absorb light at the one or more wavelengths in the voltage-dependent manner with a voltage response time of less than about 3 ms.

According to some embodiments, the voltage-sensitive protein is configured to absorb light at the one or more wavelengths in the voltage-dependent manner with a voltage response time of less than about 1 ms.

A method for measuring a membrane potential of a neuronal cell is provided. The method comprises providing the neuronal cell expressing a voltage-sensitive protein configured to absorb light at one or more wavelengths in a voltage-dependent manner; providing a photoacoustic probe comprising a laser and an ultrasound transducer; emitting, by the laser, a light signal at the one or more wavelengths to the voltage-sensitive protein, wherein the voltage-sensitive protein absorbs the light signal; receiving, by the ultrasound transducer, a photoacoustic signal from the voltage-sensitive protein in response to absorbing the light signal; and calculating, based on the photoacoustic signal, the membrane potential of the neuronal cell.

According to some embodiments, the method further comprises displaying the membrane potential on a display device.

According to some embodiments, calculating the membrane potential of the neuronal cell comprises: quantifying, based on the photoacoustic signal, at least one light absorption characteristic of the voltage-sensitive protein, wherein the at least one light absorption characteristic is configured to shift based on the membrane potential of the neuronal cell; and determining, based on the quantified at least one light absorption characteristic, the membrane potential of the neuronal cell.

According to some embodiments, providing the neuronal cell expressing a voltage-sensitive protein comprises transfecting the neuronal cell with a vector comprising a gene encoding the voltage-sensitive protein, wherein the gene is expressed by the neuronal cell.

An engineered biomaterial is provided. The engineered biomaterial comprises one or more neuronal cells, where each neuronal cell expresses a voltage-sensitive protein configured to absorb light at one or more wavelengths, wherein at least one light absorption characteristic of the voltage-sensitive protein is configured to shift based on a membrane potential of the neuronal cell.

According to some embodiments, the voltage-sensitive protein comprises a transmembrane protein. According to additional embodiments, the transmembrane protein comprises a rhodopsin.

According to some embodiments, the at least one light absorption characteristic comprises an absorption coefficient of the voltage-sensitive protein, wherein the absorption coefficient is configured to shift based on the membrane potential sensed by the voltage-sensitive protein.

According to some embodiments, the at least one light absorption characteristic comprises a peak absorption wavelength of the voltage-sensitive protein from the one or more wavelengths, wherein the peak absorption wavelength is configured to shift based on the membrane potential sensed by the voltage-sensitive protein.

According to some embodiments, the at least one light absorption characteristic comprises a total absorption value for the voltage-sensitive protein at the one or more wavelengths, wherein the total absorption value is configured to shift based on the membrane potential sensed by the voltage-sensitive protein.

According to some embodiments, each neuronal cell comprises a gene encoding the voltage-sensitive protein delivered to the neuronal cell by a vector. According to additional embodiments, the vector comprises one or more of a plasmid, a cosmid, and a virus. According to additional embodiments, the gene is delivered by the vector via transfection. According to further embodiments, the transfection comprises one of a transient transfection and a stable transfection.

According to some embodiments, the at least one light absorption characteristic of the voltage-sensitive protein is sensitive to changes in the membrane potential across a voltage range of about −70 mV to about 30 mV.

According to some embodiments, the voltage-sensitive protein has an extinction coefficient between about 102 M−1 cm−1 to about 104 M−1 cm−1.

According to some embodiments, the at least one light absorption characteristic is configured to shift based on the membrane potential with a voltage response time of less than about 3 ms.

According to some embodiments, the at least one light absorption characteristic is configured to shift based on the membrane potential with a voltage response time of less than about 1 ms.

A DNA vector for a photoacoustic voltage indicator is provided, the DNA vector comprises a gene encoding a voltage-sensitive protein configured to absorb light at one or more wavelengths, wherein at least one light absorption characteristic of the voltage-sensitive protein is configured to shift based on a membrane potential of the neuronal cell, and wherein the DNA vector is configured to be transfected to a neuronal cell.

According to some embodiments, the DNA vector comprises one or more of a plasmid, a cosmid, and a virus.

According to some embodiments, the DNA vector is configured to be transfected to the neuronal cell by one of a transient transfection and a stable transfection.

BRIEF DESCRIPTION OF THE DRAWINGS

The accompanying drawings, which are incorporated in and form a part of the specification, illustrate the embodiments of the technology and together with the written description serve to explain the principles, characteristics, and features of the technology. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope. Such aspects of the disclosure be embodied in many different forms; rather, these embodiments are provided so that this disclosure will be thorough and complete, and will fully convey its scope to those skilled in the art.

As used in this document, the singular forms "a," "an," and "the" include plural references unless the context clearly dictates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells as well as the range of values greater than or equal to 1 cell and less than or equal to 3 cells. Similarly, a group having 1-5 cells refers to groups having 1, 2, 3, 4, or 5 cells, as well as the range of values greater than or equal to 1 cell and less than or equal to 5 cells, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason.

All percentages, parts and ratios of a composition are based upon the total weight of the composition and all measurements made are at about 25° C., unless otherwise specified.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $1/10$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

It will be understood by those within the art that, in general, terms used herein are generally intended as "open"

terms (for example, the term "including" should be interpreted as "including but not limited to," the term "having" should be interpreted as "having at least," the term "includes" should be interpreted as "includes but is not limited to," et cetera). Further, the transitional term "comprising," which is synonymous with "including," "containing," or "characterized by," is inclusive or open-ended and does not exclude additional, unrecited elements or method steps. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "patient" and "subject" are interchangeable and refer to any living organism that contains neural tissue. As such, the terms "patient" and "subject" may include, but are not limited to, any non-human mammal, primate or human. A subject can be a mammal such as a primate, for example, a human. The term "subject" includes domesticated animals (e.g., cats, dogs, etc.); livestock (e.g., cattle, horses, swine, sheep, goats, etc.), and laboratory animals (e.g., mice, rabbits, rats, gerbils, guinea pigs, possums, etc.). A patient or subject may be an adult, child or infant.

The term "tissue" refers to any aggregation of similarly specialized cells that are united in the performance of a particular function.

The term "disorder" is used in this disclosure to mean, and is used interchangeably with, the terms "disease," "condition," or "illness," unless otherwise indicated.

The term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

Photoacoustic Voltage Indicators

As discussed herein, it may be desirable to detect and measure changes in membrane potential of a neuron in order to track action potentials and assess neurological activity. Evaluating neurological activity provides important information that may enhance understanding of physiological mechanisms, functional behaviors of animals, various disease states, and disease etiology. As generally described herein, membrane potential may be detected by tracking a voltage indicator that senses a voltage across the membrane and emits a voltage-specific response. Ideally, the voltage may be tracked in real time or close to real time, with high temporal resolution and high signal-to-noise ratio. Moreover, it would be useful to track membrane potential at a greater depth in order to examine neurological activity of neural networks in deeper regions of living tissue (e.g., the brain).

Accordingly, embodiments of the present subject matter are directed to a photoacoustic voltage indicator (PAVI) for tracking membrane potential of a neuron. The photoacoustic voltage indicator may be a voltage-sensitive protein expressed by a neuronal cell. For example, the voltage-sensitive protein may be a transmembrane protein configured to detect a voltage across the membrane of the neuronal cell.

As described herein, a voltage-sensitive protein may be any protein capable of detecting a voltage in an environment and having a voltage-specific response. In nature, various types of membrane proteins are voltage-sensitive proteins. For example, naturally occurring voltage-sensitive proteins may include ion channels, transporters, pumps, enzymes, and the like, each of which may detect the voltage and regulate or alter the protein's function based on a detected voltage. In some embodiments, the voltage-sensitive protein may comprise a voltage-detecting domain and an absorption domain configured to absorb light in a voltage-specific manner. In some embodiments, the voltage-detecting domain may influence or alter the absorption response of the absorption domain based on a detected voltage, thereby inducing a voltage-specific response by the absorption domain. However, in some embodiments, the voltage-detecting domain and the absorption domain may not be separate, discrete domains of the voltage-sensitive protein. Instead, one or more domains of the voltage-specific protein may function as both the voltage-detecting domain and the absorption domain. In some embodiments, the voltage-detecting ability and absorption ability of the voltage-sensitive protein may be more generally described as characteristics of the voltage-sensitive protein overall.

In a particular example, the voltage-sensitive protein that forms the PAVI as described herein may comprise a rhodopsin. For example, the voltage-sensitive protein may comprise a microbial rhodopsin. Rhodopsins are a large class of naturally occurring proteins that may serve a variety of functions, occurring as light-driven proton pumps (bacteriorhodopsins, proteorhodopsins), light-driven proton channels (channelrhodopsins), chloride pumps (halorhodopsins), photosensors (sensory rhodopsins), and the like. Rhodopsins may be characterized by several transmembrane domains and a retinilydene chromophore bound in the protein core. Accordingly, rhodopsins may be sensitive to a detected voltage in the environment and may absorb light via the chromophore in a voltage-specific manner.

In some embodiments, the voltage-sensitive protein may be a naturally occurring protein. For example, a naturally occurring voltage-sensitive protein (e.g., microbial rhodopsin) may be introduced to a cell that does not naturally express the voltage-sensitive protein (e.g., eukaryotic cells), thereby providing a PAVI for tracking membrane potential in the cell. However, in some embodiments, alternation to the naturally occurring protein may be made through genetic modifications and/or mutation to facilitate the use of the voltage-sensitive protein as a PAVI. In some embodiments, the voltage-sensitive protein may be modified to reduce or eliminate a natural function. For example, a rhodopsin may be modified to reduce or eliminate light-induced ion pumping, thereby allowing use of the voltage-sensitive protein for tracking membrane potential without altering the voltage of the cell by its natural function. In some embodiments, the voltage-sensitive protein may be modified to improve a particular characteristic or to introduce a characteristic. For example, voltage-sensitive proteins may be modified to alter the sensitivity to voltage, alter the range of voltage sensitivity, alter the range of voltage response, alter the response speed, alter characteristics of the absorption profile as further described herein, alter sensitivity to additional factors other than voltage (e.g., eliminating sensitivity to one or more additional factors), and the like. Additional types of genetic modifications and/or mutations may be performed as would be apparent to a person having an ordinary level of skill in the art.

The voltage-detecting domain of the PAVI may detect a voltage in the environment by a variety of means. In some embodiments, the voltage-detecting domain of the PAVI comprises a conserved, positively charged transmembrane region that moves or otherwise reacts in response to changes in a membrane potential. For example, ion channels may use a positively charged transmembrane region to regulate the state of the ion channel based on a detected membrane potential. In some embodiments, the voltage-detecting domain of the PAVI comprises a specific voltage-detecting motif. In some embodiments, the PAVI may transport ions across the membrane, and the voltage-detecting domain may use the transported ions to detect a voltage. Additional or alternative types of voltage-detecting domains and other means of detecting voltage are contemplated herein as would be apparent to a person having an ordinary level of skill in the art.

The absorption domain of the PAVI may take a variety of forms. In some embodiments, the absorption domain comprises a highly absorbent molecule (i.e., a chromophore) bound to the protein core and/or otherwise linked to the PAVI. Because all molecules absorb light to some degree, a wide variety of candidates is available as chromophores. As the measurement of membrane potential is based on absorbance rather than fluorescence, it is not important that the chromophore exhibits fluorescence based on the voltage detected by the PAVI. In some embodiments, the chromophore exhibits a low amount of fluorescence. In some embodiments, the chromophore exhibits no fluorescence. The chromophore may exhibit a high amount of light absorption at a particular wavelength or range of wavelengths.

In some embodiments, the chromophore comprises a polycyclic aromatic hydrocarbon. In some embodiments, the chromophore comprises an acene molecule. For example, the chromophore may comprise a tetracene, a pentacene, and/or other highly absorbent acenes as would be apparent to a person having an ordinary level of skill in the art. In some embodiments, the chromophore comprises a chromophore commonly present in rhodopsin proteins. For example, the chromophore may comprise a retinilydene. Additional or alternate types of chromophores may be evaluated and selected for their optimal characteristics through the process of directed evolution as described herein and as would be understood by a person having an ordinary level of skill in the art.

Further, the absorption domain may exhibit a substantial absorption shift based on the voltage detected by the PAVI. For example, the chromophore exhibits an absorption profile having one or more characteristics that are variable in a voltage-specific manner. In some embodiments, the one or more characteristics of the absorption profile may be variable across a range of detected voltages. For example, the one or more characteristics may be sensitive to voltages between about −70 mV and about 30 mV, i.e., a range of voltages corresponding to a range of membrane potential fluctuation in a normal neuronal cell. However, the absorption domain may be sensitive to a larger range of voltages or a smaller range of voltages. For example, it may be desirable to provide an absorption domain that is sensitive to voltages beyond the range of membrane potentials in a normal neuronal cell in order to detect abnormal fluctuations in membrane potential or other disorders in neuronal cells. Accordingly, absorption by the PAVI may shift with respect to the one or more characteristics based on a detected voltage. Therefore, the absorption of light by the PAVI may be observed, and a real-time voltage across the membrane of the neuronal cell may be calculated based on the observed absorption profile. For example, a system as further described herein may use a device that is tuned or sensitive to the absorption profile so as to quantify the absorption and thus the membrane potential.

The absorption profile may include a variety of characteristics. In some embodiments, the absorption profile includes an absorption wavelength, an absorption wavelength range, and/or a peak absorption wavelength. For example, the peak absorption wavelength of the PAVI may shift across a range of wavelengths as the membrane potential of the neuronal cells shifts through a range of voltages. In some embodiments, the absorption profile includes an amount of absorption. For example, a total amount of light absorption and/or a rate of light absorption by the PAVI may shift across a range of values as the membrane potential of the neuronal cells shifts through a range of voltages. In some embodiments, the absorption profile includes an absorption coefficient ($\mu_a$). For example, the absorption coefficient may shift across a range of values as the membrane potential of the neuronal cells shifts through a range of voltages. Accordingly, the absorption shift may comprise a shift of one of the characteristics of the absorption profile (e.g., peak absorption wavelength) or a plurality of the characteristics based on a membrane potential of the neuronal cell. Changes in the absorption profile may alter a resulting photoacoustic effect in a detectable manner.

In some embodiments, the voltage-sensitive protein comprises a single component or domain that serves as the voltage-detecting domain and the absorption domain. In some embodiments, a chromophore bound to the voltage-sensitive protein may itself be sensitive to voltage such that the chromophore undergoes a measurable shift in absorbance based on a detected voltage. For example, some chromophores found in rhodopsins are highly sensitive to changes in the electrostatic environment in a manner that causes large changes in the absorption profile.

Various additional characteristics of the PAVI may be tailored or selected through the methods described herein. In some embodiments, the PAVI may have a high extinction coefficient. For example, the extinction coefficient may be about $10^2$ to about $10^3$ $M^{-1}$ $cm^{-1}$, about $10^3$ to about $10^4$ $M^{-1}$ $cm^{-1}$, greater than about $10^4$ $M^{-1}$ $cm^{-1}$, or individual values or ranges therebetween. In some embodiments, the PAVI may have a peak absorption of about 300 nm to about 350 nm, about 350 nm to about 400 nm, about 400 nm to about 450 nm, greater than about 450 nm, or individual values or ranges therebetween. In some embodiments, the PAVI may have a fast voltage response time, thereby providing real-time information related to membrane potential and facilitating real-time monitoring thereof. For example, the voltage response time may be about 3 ms, about 2 ms, about 1 ms, about 0.5 ms, about 0.1 ms, less than about 0.1 ms, or individual values or ranges therebetween.

In some embodiments, the PAVI may be configured to be expressed at specific portions of neuronal cells (e.g., soma, dendrite, and axon). In some embodiments, one or more portions of the cell may exhibit different membrane potentials. Accordingly, it may be desired to track membrane potential at a specific portion of the neuronal cell. In a similar manner, the PAVI may be configured to be expressed at specific intracellular components, thereby facilitating tracking of a voltage at specific intracellular regions or components.

In some embodiments, a plurality of different PAVIs may be used in the manner described herein. For example, two or more PAVIs may be used, where each PAVI produces a unique absorption response or absorption profile. Accordingly, the photoacoustic feedback from each PAVI may be unique and discernable by a processor as described herein. Accordingly, multiple PAVIs may be used for greater accuracy and/or validation of the membrane potential through redundant track. A processor of a system as further described herein may distinguish between the PAVIs based on the unique photoacoustic feedback.

In some embodiments, a plurality of PAVIs may be used to track membrane potential and a plurality of portions of the neuronal cell (e.g., soma, dendrite, and axon) or intracellular components. As described, each PAVI may have a unique absorption response or absorption profile resulting in unique photoacoustic feedback from each PAVI. Accordingly, a system as further described herein may be configured to detect photoacoustic feedback from each PAVI separately and thus quantify membrane potential of each portion of the neuronal cell. As such, this mix of PAVIs facilitates more specific tracking of membrane potentials and the progression of action potentials. For example, in addition to changes in overall membrane potential, information about the degree of fluctuation, the manner of fluctuation, and/or the timing of such fluctuation at each portion of the neuronal cell may provide information about the mechanism and/or behavior in different disease states.

The PAVIs may be loaded to the neuron cell in a variety of manners. In some embodiments, transfection techniques may be used to deliver a gene encoding the voltage-sensitive protein to neuronal cells. For example, a vector (i.e., a carrier DNA molecule) comprising the gene and/or additional nucleic acid sequences required for expression of the gene may be introduced to the neuronal cells. For example, vectors may be inserted within a pipette that is invasively inserted into the tissue to inject the vectors therein. However, in some embodiments, the vectors are applied to the tissue and uptake may occur passively or by another actively applied stimulus. In some embodiments, the vector comprises a plasmid. In some embodiments, the vector comprises a cosmid. In some embodiments, the vector comprises a virus.

In some embodiments, the voltage-sensitive protein may be transiently expressed (i.e., through transient transfection) in the neuronal cells. In some embodiments, the voltage-sensitive protein may be stably expressed (i.e., through stable expression) such that the gene is incorporated in the genome of the neuronal cell and passed through cell reproduction, thereby providing a cell culture or cell line that expresses the voltage-sensitive protein.

In some embodiments, the voltage-sensitive proteins may be tuned and/or selected through directed evolution techniques. In some embodiments, an expression vector for the voltage-sensitive protein may be used to develop a mutagenesis library, i.e., a library comprising a plurality of randomly mutated variations of the expression vector. For example, a mutagenesis library may be developed using an error-prone polymerase chain reaction (PCR) technique. In some embodiments, a mutagenesis library may include 10,000 variations of the expression vector, 100,000 variations of the expression vector, or greater than 100,000 variations of the expression vector. A mutagenesis library may be screened for particular desired characteristics to identify a particularly suitable expression vector. In some embodiments, the mutagenesis library of voltage-sensitive proteins may be screened for membrane localization, absorption characteristics, photoacoustic response characteristics, sensitivity to voltage, range of voltage sensitivity, range of voltage response, voltage response speed, and the like. In some embodiments, photoacoustic microscopy and/or patch clamp electrophysiology (e.g., whole-cell patch clamp electrophysiology) may be used to assess and screen the mutagenesis library. Accordingly, one or more ideal voltage-sensitive proteins may be identified for tracking of membrane potential in a cell.

System for Measuring Membrane Potential of a Neuron

Figure 1:
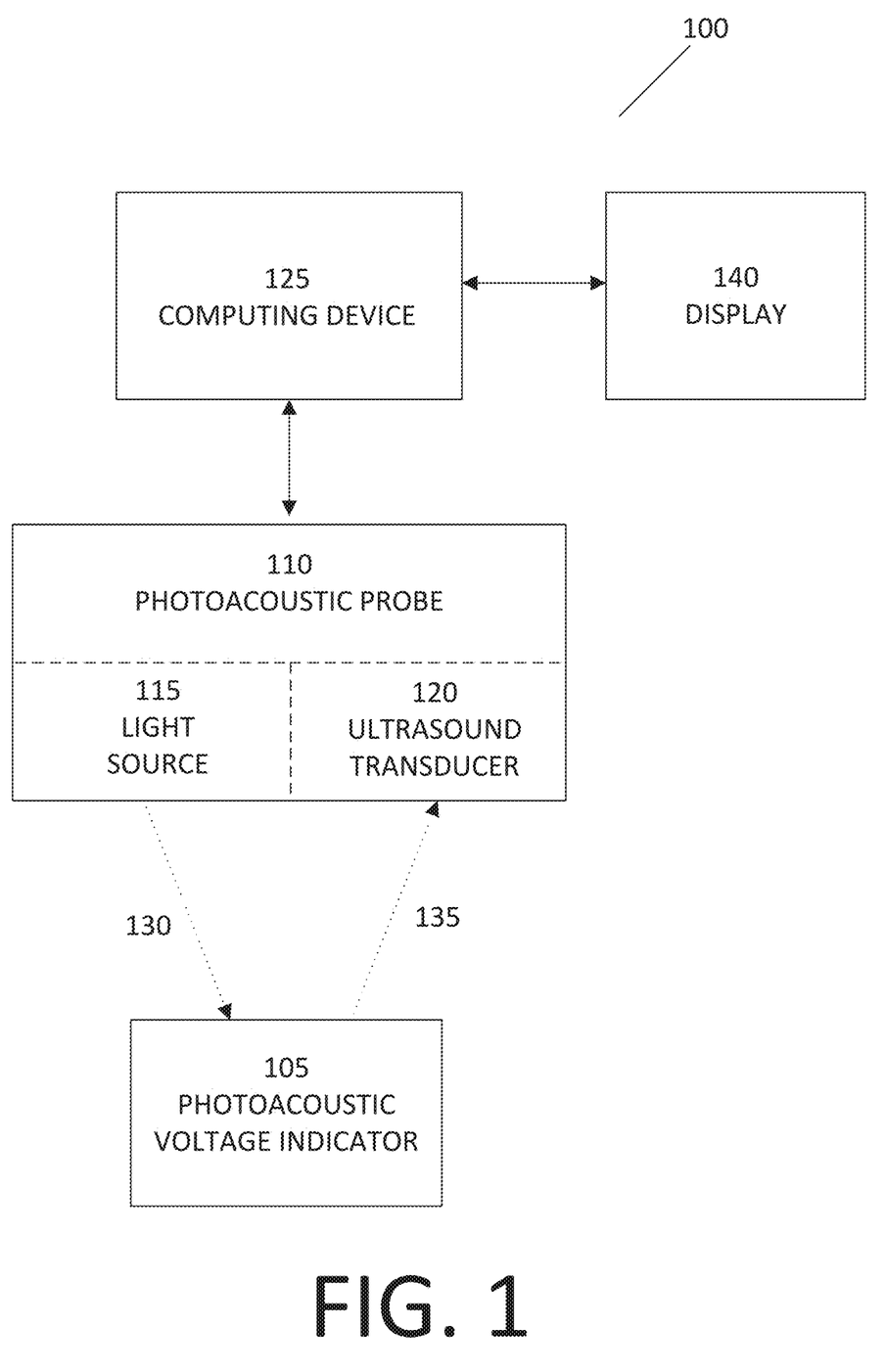
FIG. 1 illustrates a block diagram of an illustrative system for measuring membrane potential of a neuron in accordance with an embodiment.

In another aspect of the present subject matter, a system for measuring the membrane potential of a neuron is disclosed. Referring now to FIG. 1, the system 100 comprises a neuronal cell expressing a photoacoustic voltage indicator 105 as described herein for tracking membrane potential. The photoacoustic voltage indicator 105 may be a voltage-sensitive protein configured to detect a voltage and absorb light in a voltage-specific manner as described. The system 100 further comprises a photoacoustic probe 110 comprising a light source 115 configured to emit a light signal 130 and an ultrasound transducer 120 configured to receive a photoacoustic signal 135 in response to the emitted light signal. The system 100 further comprises a computing device 125 configured to receive the photoacoustic signal 135 from the ultrasound transducer 120 and calculate, based on the photoacoustic signal 135, a membrane potential of the neuron. In some embodiments, the system may further comprise a display 140 configured to receive the membrane potential from the computing device 125 and display the membrane potential to a user.

Figure 2A:
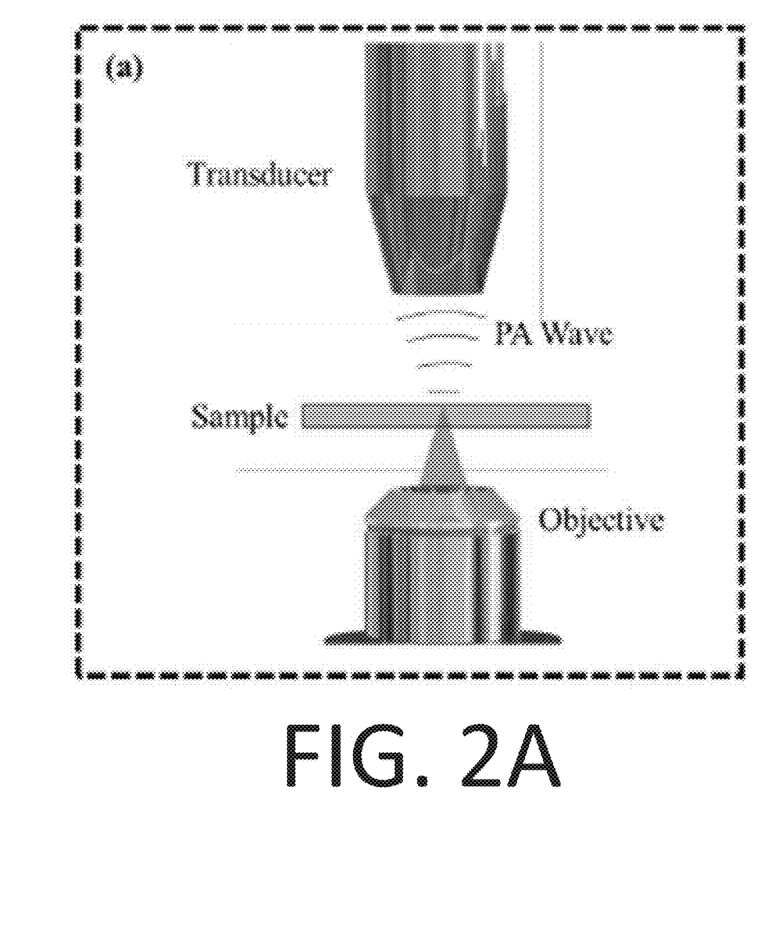
FIGS. 2A-2B depict exemplary embodiments of photoacoustic probes in accordance with some embodiments.
Figure 2B:
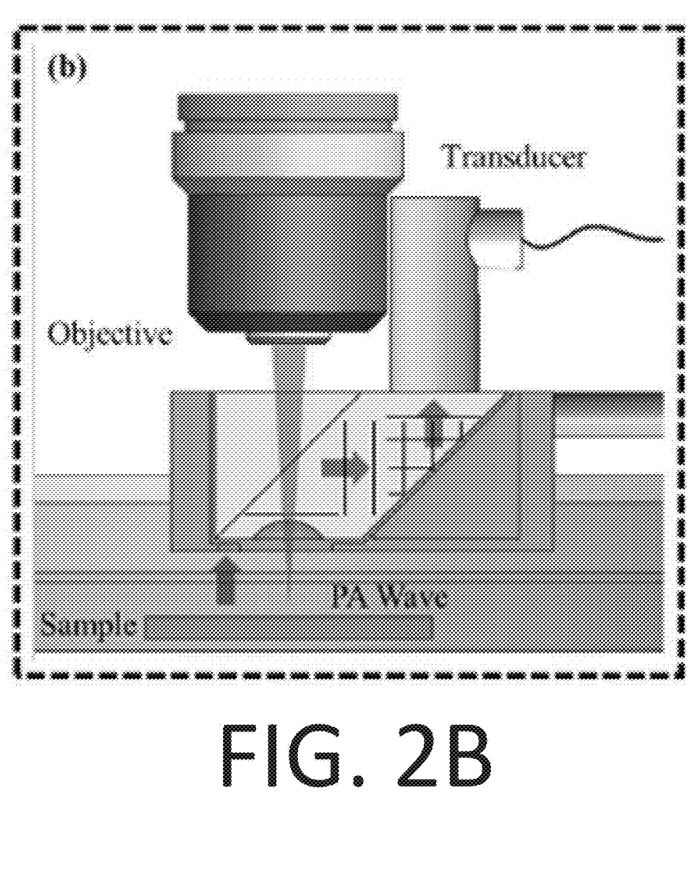

The photoacoustic probe 110 may be provided in a variety of forms. In some embodiments, the photoacoustic probe uses a high-frequency ultrasound transducer. In some embodiments, the photoacoustic probe 110 may be a photoacoustic microscopy device. For example, the photoacoustic probe 110 may be an optical resolution photoacoustic microscopy (OR-PAM) device. For example, the photoacoustic probe may be configured to detect changes in refractive index in the tissue may be used to sense the photoacoustic signal 135 because the photoacoustic signal 135 results in a change in refractive index of the material that it propagates through. In some embodiments, differential interference contrast microscopy and/or Brillouin microscopy is used. An exemplary OR-PAM arrangement is depicted in FIG. 2A. However, in some embodiments, the photoacoustic probe 110 may be an acoustic resolution photoacoustic microscopy (AR-PAM) device. The photoacoustic probe is designed to emit the light signal and receive the photoacoustic signal from the same side. An exemplary AR-PAM arrangement is depicted in FIG. 2B.

In some embodiments, the light source 115 is a laser. For example, the light source 115 may be a high-intensity laser, e.g., a nanosecond pulsed laser beam. The laser may be configured to provide fast excitation and resultant photoacoustic signal. For example, the laser may be a Bessel beam laser. However, the light source 115 may also be provided in a variety of additional forms as would be understood to a person having an ordinary level of skill in the art. In some embodiments, the photoacoustic probe 110 may further comprise a reflective surface (e.g., a mirror) to direct the light signal away from the photoacoustic probe 110 (e.g., through an aperture) and towards the tissue. In some embodiments, the reflective surface may be movable to adjust the direction of the light signal.

In some embodiments, the photoacoustic probe includes additional components. In some embodiments, the photoacoustic probe includes an ultrasound transmission line, a light transmission line, an ultrasound receiver, and/or an amplifier. In some embodiments, the photoacoustic probe includes a plurality of a described component. For example, the photoacoustic probe may include a plurality of ultrasound transducers and/or lasers.

The computing device 125 is configured to receive the photoacoustic signal 135 and calculate the membrane potential. This is performed based on the known and understood principles of the photoacoustic effect. In essence, the emitted light signal creates a resultant sound signal. When molecules (i.e., the chromophores or other absorption domains of the PAVIs) absorb light at specific wavelengths, the result is a molecular excitation and thermal expansion of the tissue that generates an acoustic wave. The computing device 125 may receive several parameters through input and/or calibration in order to calculate the membrane potential. Particularly, the computing device 125 may have information related to the absorption shift of the voltage-sensitive protein. As such, the computing device (or alternatively, the photoacoustic probe) is tuned to identify a voltage-dependent characteristic of the absorption profile (e.g., a peak absorption wavelength, a total amount of absorption, an absorption coefficient, etc.) based on the known absorption shift. For example, the initial pressure wave ($P_0$) of the photoacoustic signal may be expressed as:

$$P_0 = \Gamma \mu_\alpha(\lambda) F$$

where $\Gamma$ is the Grüneisen parameter, $\mu_\alpha$ is the absorption coefficient for a particular wavelength $\lambda$ of emitted light, and F is the fluence. Shifts in $\mu_\alpha$ (i.e., the absorption shift) results in changes to the pressure wave (i.e., the photoacoustic signal). By measuring the changes to the photoacoustic signal, a degree of change in voltage within the cell may be calculated, thereby providing a measure for membrane potential. A larger absorption shift by the PAVI may be indicative of a larger change in membrane potential within the cell. Similarly, a larger change in the photoacoustic signal is indicative of a larger change in membrane potential.

In some embodiments, the computing device 125 and/or the display 140 may be used to record and monitor membrane potential in real time. For example, the system 100 may be used to repeatedly collect measurements over a period of time and may be displayed and updated in real time. In some embodiments, a stimulus may be applied to the tissue or another test may be performed during collection of measurements in order to record a response. In some embodiments, a drug, a biologic, or a chemopharmaceutical may be applied to the tissue in order to record an effect of the drug, biologic, or chemopharmaceutical on the behavior of the neurons (e.g., firing patterns).

Method of Measuring Membrane Potential of a Neuron

Figure 3:
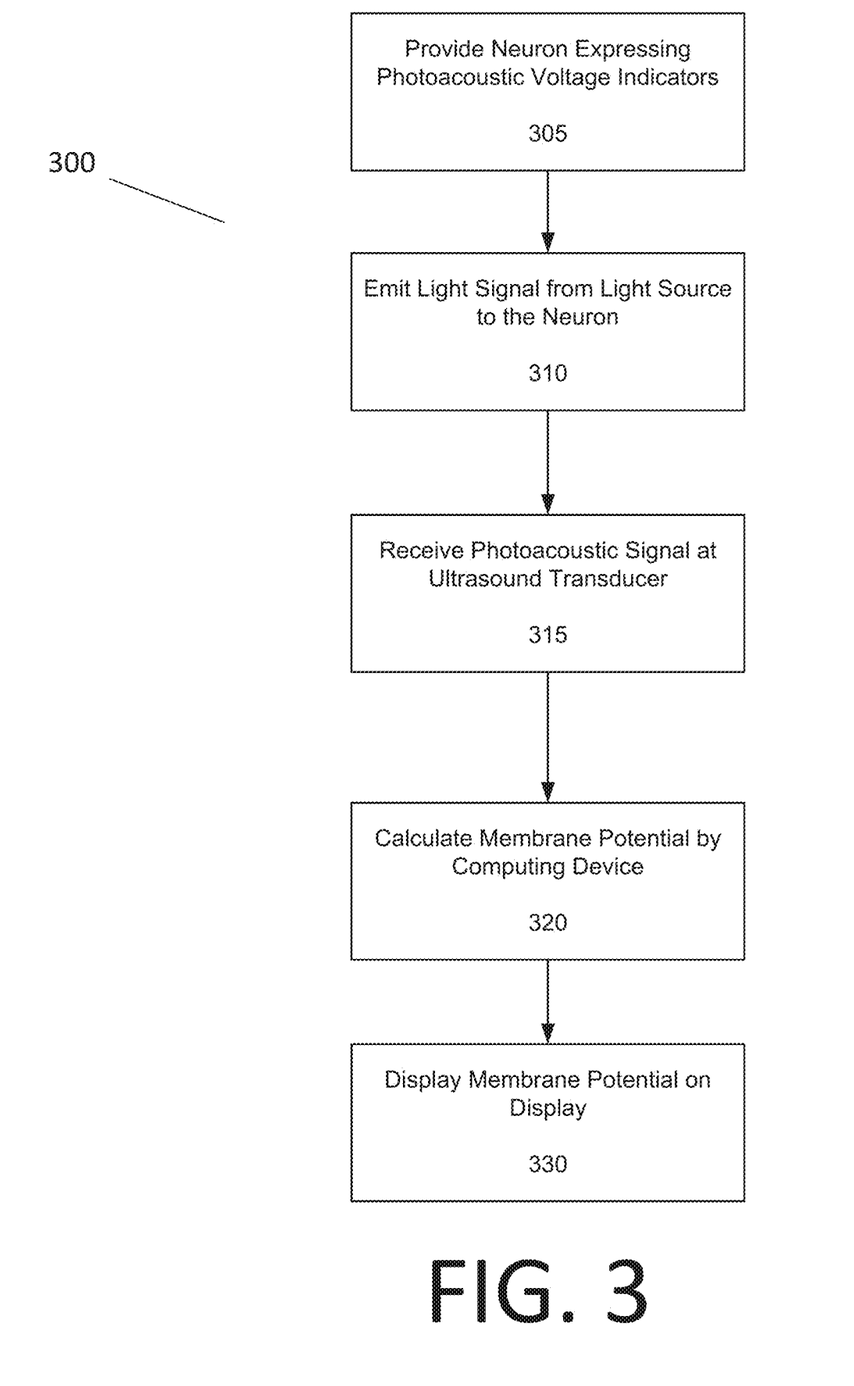
FIG. 3 depicts a flow diagram of an illustrative method of measuring the membrane potential of a neuron in accordance with an embodiment.

In another aspect of the present subject matter, a method of measuring the membrane potential of a neuron is disclosed. The method 300 comprises providing 305 a neuron expressing a photoacoustic voltage indicator into the neuron, wherein the photoacoustic voltage indicator comprises a voltage-sensitive protein configured to absorb light at a first wavelength in a voltage-dependent manner as described herein. The PAVI may comprise any of the embodiments and/or characteristics as described herein. The method further comprises emitting 310 a light signal to the neuron by a light source of a photoacoustic probe and receiving 315 a photoacoustic signal by an ultrasound transducer of the photoacoustic probe in response to the light signal. The method further comprises receiving the photoacoustic signal by a computing device and calculating 320 the membrane potential of the neuron based on the photoacoustic signal.

In some embodiments, the method comprises calculating the membrane potential of a single cell. In some embodiments, the method comprises calculating the membrane potential of a plurality of cells. For example, a plurality of simultaneously firing neurons may be tracked by the method described herein. In some embodiments, the method comprises monitoring the membrane potential of one or more cells over a period of time. For example, the method may be repeated several times over a short duration in order to track the behavior of the cells through the stages of the action potential mechanism.

In some embodiments, the method further comprising displaying 330 the calculated membrane potential on a display connected to the computing device. In some embodiments, additional information may be displayed on the computing device. For example, where a plurality of measurements have been collected, the measurements may be displayed in an aggregate form, such as a chart, graphic, table, profile, or other format.

In some embodiments, the computing device and/or the display may be used to record and monitor membrane potential in real time. For example, the system may be used to repeatedly collect measurements over a period of time and may be displayed and updated in real time. In some embodiments, a stimulus may be applied to the tissue or another test may be performed during collection of measurements in order to record a response. In some embodiments, a drug, a biologic, or a chemopharmaceutical may be applied to the tissue in order to record an effect of the drug, biologic, or chemopharmaceutical on the behavior of the neurons (e.g., firing patterns).

In some embodiments, the method is used in vitro for research or testing purposes. However, in additional embodiments, the method may be used in vivo to record the behavior of live tissue. For example, the method may be used on a subject, such as a mouse, other laboratory animals, or a human. The method may be used to study neural mechanisms, neural diseases and disorders, and/or to study neurological behavior of animals. In some embodiments, the method may be used in clinical settings, for example for diagnosing conditions in patients and/or evaluating a subject's behavior.

While the described embodiments are discussed with respect to tracking the action potential in neurons, the apparatuses, systems, and methods described herein may be adapted for other types of cells that exhibit a fluctuating membrane potential as would be apparent to a person having an ordinary level of skill in the art. For example, the apparatuses, systems, and methods may be adapted to track the action potential of cardiomyocytes to evaluate cardiovascular activity and health.

Data Processing Systems for Implementing Embodiments Herein

Figure 4:
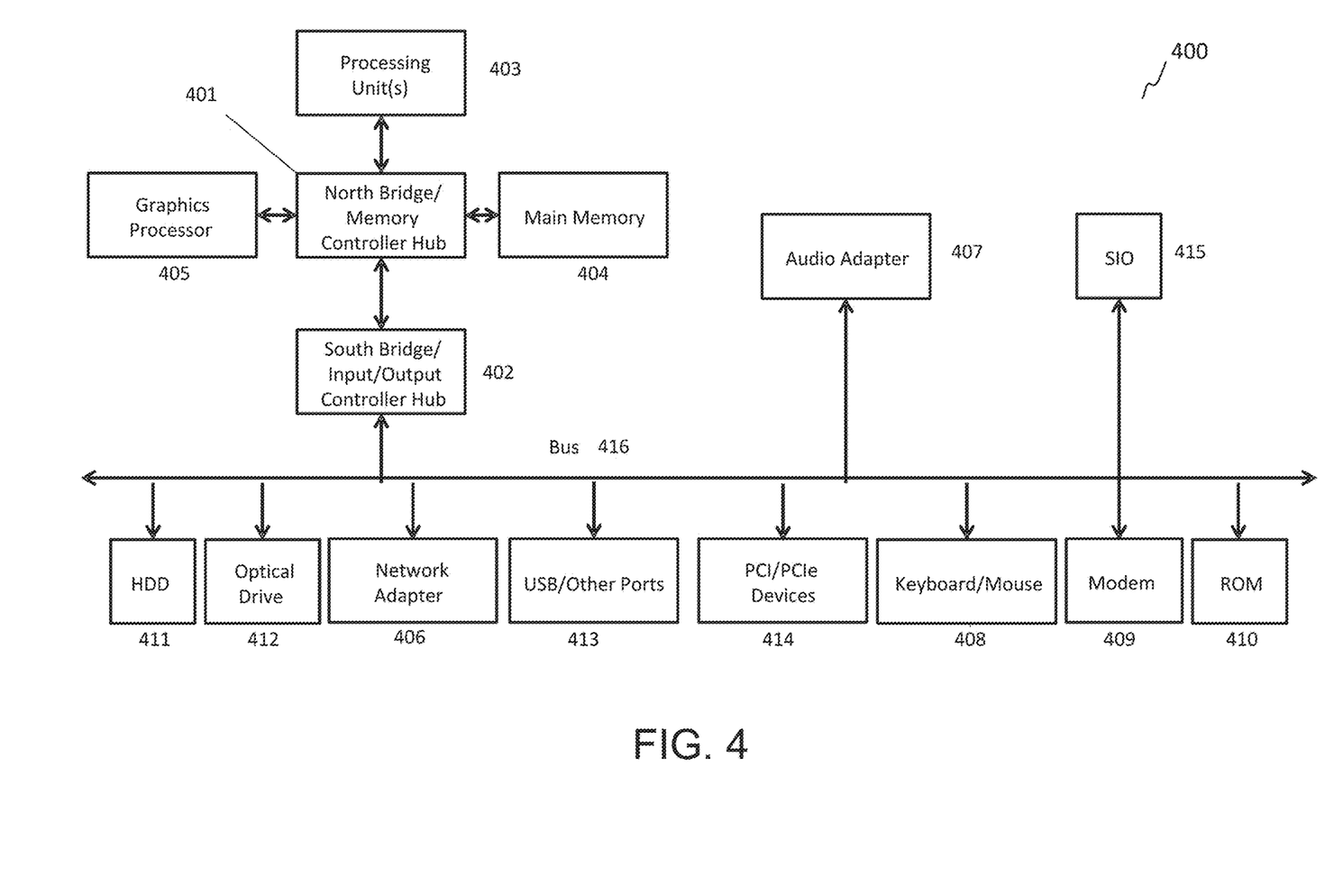
FIG. 4 illustrates a block diagram of an illustrative data processing system in which aspects of the illustrative embodiments are implemented.

FIG. 4 illustrates a block diagram of an illustrative data processing system 400 in which aspects of the illustrative embodiments are implemented. The data processing system 400 is an example of a computer, such as a server or client, in which computer usable code or instructions implementing the process for illustrative embodiments of the present technology are located. In some embodiments, the data processing system 400 may be a server computing device. For example, data processing system 400 can be implemented in a server or another similar computing device. The data processing system 400 can be configured to, for example, transmit and receive information related to the light signal, photoacoustic signal and/or membrane potential.

In the depicted example, data processing system 400 can employ a hub architecture including a north bridge and memory controller hub (NB/MCH) 401 and south bridge and input/output (I/O) controller hub (SB/ICH) 402. Processing unit 403, main memory 404, and graphics processor 405 can be connected to the NB/MCH 401. Graphics processor 405 can be connected to the NB/MCH 401 through, for example, an accelerated graphics port (AGP).

In the depicted example, a network adapter 406 connects to the SB/ICH 402. An audio adapter 407, keyboard and mouse adapter 408, modem 409, read only memory (ROM) 410, hard disk drive (HDD) 411, optical drive (e.g., CD or DVD) 412, universal serial bus (USB) ports and other communication ports 413, and PCI/PCIe devices 414 may connect to the SB/ICH 402 through bus system 416. PCI/PCIe devices 414 may include Ethernet adapters, add-in cards, and PC cards for notebook computers. ROM 410 may be, for example, a flash basic input/output system (BIOS). The HDD 411 and optical drive 412 can use an integrated drive electronics (IDE) or serial advanced technology attachment (SATA) interface. A super I/O (SIO) device 415 can be connected to the SB/ICH 402.

An operating system can run on the processing unit 403. The operating system can coordinate and provide control of various components within the data processing system 400. As a client, the operating system can be a commercially available operating system. An object-oriented programming system, such as the Java™ programming system, may run in conjunction with the operating system and provide calls to the operating system from the object-oriented programs or applications executing on the data processing system 400. As a server, the data processing system 400 can be an IBM® eServer™ System® running the Advanced Interactive Executive operating system or the Linux operating system. The data processing system 400 can be a symmetric multiprocessor (SMP) system that can include a plurality of processors in the processing unit 403. Alternatively, a single processor system may be employed.

Instructions for the operating system, the object-oriented programming system, and applications or programs are located on storage devices, such as the HDD 411, and are loaded into the main memory 404 for execution by the processing unit 403. The processes for embodiments described herein can be performed by the processing unit 403 using computer usable program code, which can be located in a memory such as, for example, main memory 404, ROM 410, or in one or more peripheral devices.

A bus system 416 can be comprised of one or more busses. The bus system 416 can be implemented using any type of communication fabric or architecture that can provide for a transfer of data between different components or devices attached to the fabric or architecture. A communication unit such as the modem 409 or the network adapter 406 can include one or more devices that can be used to transmit and receive data.

Those of ordinary skill in the art will appreciate that the hardware depicted in FIG. 4 may vary depending on the implementation. Other internal hardware or peripheral devices, such as flash memory, equivalent non-volatile memory, or optical disk drives may be used in addition to or in place of the hardware depicted. Moreover, the data processing system 400 can take the form of any of a number of different data processing systems, including but not limited to, client computing devices, server computing devices, tablet computers, laptop computers, telephone or other communication devices, personal digital assistants, and the like. Essentially, data processing system 400 can be any known or later developed data processing system without architectural limitation.

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples:

EXAMPLES

Example 1—Development of PAM Systems to Measure Absorption Shifts in PAVIs

Photoacoustic microscopy (PAM) systems typically involve raster scanning optical and acoustic focal points, which are confocally aligned. Systems are categorized as optical resolution (OR-PAM) or acoustic resolution (AR-PAM) as determined by the sharper focal point. These systems will be investigated for in vitro and in vivo applications.

Example 1.1—Investigation of Photoacoustic Wave Generation and Detection

Methods.

The frame rate required to visualize multiple simultaneously firing neurons will provide major challenges to most reported PAM systems, emphasizing a need for faster excitation and detection. Compared to point scanning or full sample illumination, Bessel beams may provide a successful method for fast signal generation over a 3D volume while still maintaining high resolution. Easily replicable light sheet microscopy systems retrofitted with high frequency transducer arrays in combination with existing time reversal algorithms may allow for the development of high-speed PAM systems capable of detecting changes in membrane potential across several neurons. These methods will be tested to evaluate frame rate and determine feasibility.

Photoacoustic waves change the refractive index of the material through which they propagate. Two different optical techniques may be capable of detecting these changes in the refractive index including differential interference contrast (DIC) microscopy and Brillouin microscopy. These optical techniques will be tested to evaluate sensitivity to refractive index and determine feasibility.

Anticipated Results. Testing of the potential methods and techniques described will yield a PAM system with the requisite frame rate and sensitivity to detect fluctuations in membrane potential.

Example 1.2—Development of OR-PAM System for Monitoring Action Potentials

Methods. An OR-PAM system will be designed and assessed in terms of frame rate to determine whether it is capable of monitoring single cells in culture (i.e., in vitro imaging). The system may be designed with a light source and a transducer on opposing sides of the culture sample. A potential OR-PAM system configuration is illustrated in FIG. 2A.

Anticipated Results.

Development and assessment of OR-PAM systems will yield an OR-PAM system with the requisite resolution to monitor single cells in in vitro cultures and the requisite sensitivity to detect fluctuations in membrane potential.

Example 1.3—Development of AR-PAM System for Monitoring Action Potentials

Methods.

An AR-PAM system will be designed and assessed in terms of frame rate to determine whether it is capable of visualizing multiple simultaneously firing neurons in in vivo environments as well as in vitro environments. The system must be capable of confocal optical and acoustic alignment from the same side of the tissue or sample. A potential AR-PAM system configuration is illustrated in FIG. 2B.

Anticipated Results.

Development and assessment of OR-PAM systems will yield an OR-PAM system with the requisite resolution to monitor neurons in vivo and the requisite sensitivity to detect fluctuations in membrane potential.

Example 2—Development of PAVIs for Tracking Membrane Potential

Absorption-based PAVIs will be synthesized to determine membrane potential in neuronal cells based on the photoacoustic effect. Several voltage-sensitive transmembrane proteins will be developed and assessed for several properties to determine feasibility.

Example 2.1—Development of PAVIs

Methods.

Directed evolution will be used to engineer transmembrane voltage indicators optimized for photoacoustic applications. Directed evolution has been previously used for development of fluorescent transmembrane voltage indicators. A mutagenesis library ($10^5$ will be developed via error-prone PCR of existing genetically encoded voltage indicators (GEVIs). The GEVIs of the mutagenesis library may be transfected into excitable cells. Single cell analysis through photoacoustic microscopy and patch clamp electrophysiology may be used to assess the GEVIs of the mutagenesis library.

Anticipated Results.

Directed evolution as described will provide rapid development of GEVIs with various desirable characteristics for photoacoustic applications, thereby providing PAVI candidates for screening.

Example 2.2—Screening of PAVIs for Optimal Characteristics

Methods.

Synthesized PAVIs will be screened with the following criteria: (1) extinction coefficient $>10^3$ $M^{-1}$ $cm^{-1}$; voltage sensitivity with in at least the range of −70 my to 30 mv; and voltage response time <1 ms. GEVIs from the mutagenesis library will be screened for each characteristic to identify PAVIs with optimized characteristics.

Anticipated Results.

Screening of the PAVIs as described will yield one or more PAVIs meeting all criteria. The PAVIs will demonstrate an ability to produce signals that monitor change in photoacoustic signal in a manner comparable or greater than currently available fluorescent voltage indicators.

Example 2.3—Automated System for Directed Evolution of Highly Absorbing PAVIs Methods.

A computerized system will be developed for automated screening of neuronal cells producing the largest photoacoustic signal. The computerizing system will rely on robotic photoacoustic guided electrophysiology techniques to assess the neuronal cells and identify optimized candidates for photoacoustic applications. The automated approach will be compared to currently available fluorescent systems used for screening in directed evolution.

Anticipated Results.

The computerized system will provide a new molecular tool for visualizing the behavior of neurons over a larger volume. The automated system will be capable of screening PAVIs in a manner comparable to or better than currently available fluorescent systems in terms of accuracy and/or efficiency.

Example 2.4—Using PAVIs for Measuring Changes in Membrane Potential

Methods.

PAVIs can be loaded and expressed in neuronal cells through using vectors and transfection techniques. The ability of PAVIs to relate changes in membrane potential will be compared to currently available fluorescent voltage indicators.

Anticipated Results.

Testing of the PAVIs for measuring changes in membrane potential will reveal that PAVIs meeting all criteria are viable tools for monitoring changes in membrane potential with accuracy comparable to or better than currently available fluorescent voltage indicators.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for measuring a membrane potential, the system comprising:
    a photoacoustic probe comprising:
        a laser configured to emit a light signal at one or more wavelengths to a neuronal cell comprising a voltage-sensitive protein capable of absorbing the light signal in a voltage-dependent manner, and
        an ultrasound transducer configured to receive a photoacoustic signal from the voltage-sensitive protein in response to absorbing the light signal;
    a processor; and
    a non-transitory, computer-readable medium storing instructions that, when executed, cause the processor to:
        receive the photoacoustic signal from the ultrasound transducer, and
        calculate, based on the photoacoustic signal, the membrane potential of the neuronal cell.

2. The system of claim 1, wherein the voltage-sensitive protein comprises a transmembrane protein.

3. The system of claim 2, wherein the transmembrane protein comprises a rhodopsin.

4. The system of claim 1, wherein at least one light absorption characteristic of the voltage-sensitive protein is configured to shift based on the membrane potential of the neuronal cell,
    wherein the instructions that cause the processor to calculate a membrane potential of the neuronal cell comprise instructions that, when executed, cause the processor to:
        quantify, based on the photoacoustic signal, the at least one light absorption characteristic of the voltage-sensitive protein, and
        determine, based on the quantified at least one light absorption characteristic, the membrane potential of the neuronal cell.

5. The system of claim 4, wherein the at least one light absorption characteristic comprises an absorption coefficient of the voltage-sensitive protein;
    wherein the absorption coefficient is configured to shift based on the membrane potential sensed by the voltage-sensitive protein.

6. The system of claim 4, wherein the at least one light absorption characteristic comprises a peak absorption wavelength of the voltage-sensitive protein from the one or more wavelengths,
    wherein the peak absorption wavelength is configured to shift based on the membrane potential sensed by the voltage-sensitive protein.

7. The system of claim 4, wherein the at least one light absorption characteristic comprises a total absorption value for the voltage-sensitive protein at the one or more wavelengths,
    wherein the total absorption value is configured to shift based on the membrane potential sensed by the voltage-sensitive protein.

8. The system of claim 1, wherein the voltage-sensitive protein is configured to absorb light at the one or more wavelengths in the voltage-dependent manner with sensitivity to changes in the membrane potential across a voltage range of about −70 mV to about 30 mV.

9. The system of claim 1, wherein the voltage-sensitive protein has an extinction coefficient between about $10^2$ $M^{-1}$ $cm^{-1}$ to about $10^4$ $M^{-1}$ $cm^{-1}$.

10. The system of claim 1, wherein the voltage-sensitive protein is configured to absorb light at the one or more wavelengths in the voltage-dependent manner with a voltage response time of less than about 3 ms.

11. The device of claim 1, wherein the voltage-sensitive protein is configured to absorb light at the one or more wavelengths in the voltage-dependent manner with a voltage response time of less than about 1 ms.

12. A method for measuring a membrane potential of a neuronal cell, the method comprising:
    providing the neuronal cell expressing a voltage-sensitive protein configured to absorb light at one or more wavelengths in a voltage-dependent manner;
    providing a photoacoustic probe comprising a laser and an ultrasound transducer;
    emitting, by the laser, a light signal at the one or more wavelengths to the voltage-sensitive protein, wherein the voltage-sensitive protein absorbs the light signal;
    receiving, by the ultrasound transducer, a photoacoustic signal from the voltage-sensitive protein in response to absorbing the light signal; and
    calculating, based on the photoacoustic signal, the membrane potential of the neuronal cell.

13. The method of claim 12, further comprising displaying the membrane potential on a display device.

14. The method of claim 12, wherein calculating the membrane potential of the neuronal cell comprises:
    quantifying, based on the photoacoustic signal, at least one light absorption characteristic of the voltage-sensitive protein, wherein the at least one light absorption characteristic is configured to shift based on the membrane potential of the neuronal cell; and
    determining, based on the quantified at least one light absorption characteristic, the membrane potential of the neuronal cell.

15. The method of claim 12, wherein providing the neuronal cell expressing a voltage-sensitive protein comprises transfecting the neuronal cell with a vector comprising a gene encoding the voltage-sensitive protein, wherein the gene is expressed by the neuronal cell.

* * * * *